(12) United States Patent
Boze et al.

(10) Patent No.: US 8,541,036 B2
(45) Date of Patent: Sep. 24, 2013

(54) SYNERGETIC EFFECT OF THE PHYTASE COMBINATION ON THE HYDROLYSIS OF PHYTIC ACID

(75) Inventors: Helene Boze, Montpellier (FR); Guy Moulin, Montferrier sur Lez (FR)

(73) Assignee: Adisseo France S.A.S., Antony (FR)

( * ) Notice: Subject to any disclaimer, the term of this patent is extended or adjusted under 35 U.S.C. 154(b) by 926 days.

(21) Appl. No.: 11/988,403

(22) PCT Filed: Jul. 7, 2006

(86) PCT No.: PCT/FR2006/001652
§ 371 (c)(1),
(2), (4) Date: Apr. 15, 2008

(87) PCT Pub. No.: WO2007/006952
PCT Pub. Date: Jan. 18, 2007

(65) Prior Publication Data
US 2010/0278965 A1    Nov. 4, 2010

(30) Foreign Application Priority Data

Jul. 8, 2005    (FR) .................................... 05 07335

(51) Int. Cl.
*C12N 9/16*    (2006.01)
(52) U.S. Cl.
USPC ................. 426/2; 426/61; 435/196; 435/105; 435/168

(58) Field of Classification Search
USPC .................. 426/2, 61; 435/196, 105, 168
See application file for complete search history.

(56) References Cited

U.S. PATENT DOCUMENTS 5,830,732 A * 11/1998 Mochizuki et al. ........... 435/195
6,183,740 B1    2/2001 Short et al.

FOREIGN PATENT DOCUMENTS

| EP | 0 619 369 A1 | | 4/1993 |
|---|---|---|---|
| EP | 0 699 762 A2 | | 3/1996 |
| EP | 0 420 358 | * | 5/1999 |
| EP | 0 931 837 | | 7/1999 |
| WO | WO 98/30681 A1 | | 7/1998 |
| WO | WO 00/71728 A1 | | 11/2000 |
| WO | WO 01/83763 A2 | | 11/2001 |
| WO | WO 02/098442 A2 | | 12/2002 |
| WO | WO 03/054199 A2 | | 7/2003 |

OTHER PUBLICATIONS

Segueilha et al.. "Purification and Properties of the Phytase from *Schwanniomyces castellii*", *Journal of Fermentation and Bioengineering*, vol. 74, No. 1, pp. 7-11, 1992.
Van Hartingsveldt et al., "Cloning, characterization and overexpression of the phytase-encoding gene (*phyA*) of *Aspergillus niger*", *Gene*, 127, pp. 87-94, 1993.
Lassen et al., "Expression, Gene Cloning, and Characterization of Five Novel Phytases from Four Basidiomycete Fungi: *Peniophora lycii, Agrocybe pediades*, a *Ceriporia* sp., and *Trametes pubescens*", *Applied and Environmental Microbiology*, pp. 4701-4707, Oct. 2001.
Ullah et al., "*PhyA* gene product of *Aspergillus ficuum* and *Peniophora lycii* produces dissimilar phytases", *Biochemical and Biophysical Research Communications*, 303 pp. 463-468, 2003.
Nakano et al., "The Pathway of Dephosphorylation of *myo*-Inositol Hexakisphosphate by Phytases from Wheat Bran of *Triticum aestivum* L. cv. Nourin #61", Biosci. Biotechnol. Biochem., 64 (5), pp. 995-1003, 2000.
Fujita, Jin et al., "Critical Importance of Phytase for Yeast Growth and Alcohol Fermentation in Japanese *sake* Brewing," *Biotechnology Letters*, 2001, pp. 867-871, vol. 23.
Näsi, M. et al., "Comparison of *Aspergillus niger* Phytase and *Trichoderma reesei* Phytase and Acid Phosphatase on Phytate Phosphorous Availability in Pigs Fed on Maize-Soybean Meal or Barley-Soybean Meal Diets," *Arch. Animal Nutr.*, 1999, pp. 15-27, vol. 52.
Zyta, K., "The role of Acid Phosphatase Activity During Enzymic Dephosphorylation of Phytates by *Apergillus niger* Phytase," *World Journal of Microbiology and Biotechnology*, 1993, pp. 117-119, vol. 9.
Wyss, Markus et al., "Biochemical Characterization of Fungal Phytases (*myo*-Inositol Hexakisphosphate Phosphohydrolases): Catalytic Properties," *Applied and Enviromental Microbiology*, Feb. 1999, pp. 367-373, vol. 65, No. 2.
Dvořáková, J. et al., "Phytase: Sources, Preparation and Exploitation," *Folia Microbiol.*, 1998, pp. 323-338, vol. 43, No. 4.
Vohra, Ashima et al., "Phytases: Microbial Sources, Production, Purification, and Potential Biotechnological Applications," *Critical Reviews in Biotechnology*, 2003, pp. 29-60, vol. 23, No. 1.
International Search Report issued in International Application No. PCT/FR2006/001652 dated Nov. 29, 2006 (with translation).

* cited by examiner

*Primary Examiner* — D. Lawrence Tarazano
*Assistant Examiner* — Hamid R Badr
(74) *Attorney, Agent, or Firm* — Oliff & Berridge, PLC.

(57) ABSTRACT

The invention concerns compositions and methods combining at least two phytases for hydrolyzing phytic acid (myo-inositol hexakis phosphate) into inorganic monophosphates, into myo-inositols with lower degree of phosphorylation and into free myo-inositol. Said compositions and methods are of particular interest for animal feeding.

27 Claims, 3 Drawing Sheets

A) B)

SEQUENCE LISTING

<160> NUMBER OF SEQ ID NOS: 7

<210> SEQ ID NO 1
<211> LENGTH: 461
<212> TYPE: PRT
<213> ORGANISM: Schwanniomyces castellii (Debaryomyces occidentalis)

<400> SEQUENCE: 1

```
Met Val Ser Ile Ser Lys Leu Ile Asn Asn Gly Leu Leu Ala Gly
 1               5                  10                  15

Gln Ser Val Tyr Gln Asp Leu Ala Thr Pro Gln Gln Ser Val Glu
            20                  25                  30

Gln Tyr Asn Ile Ile Arg Phe Leu Gly Gly Ser Gly Pro Tyr Ile Gln
            35                  40                  45

Arg Ser Gly Tyr Gly Ile Ser Thr Asp Ile Pro Asp Gln Cys Thr Ile
50                   55                  60

Lys Gln Val Gln Leu Met Ser Arg His Gly Glu Arg Tyr Pro Ser Lys
65                   70                  75                  80

Asn Ser Gly Lys Lys Leu Lys Thr Ile Tyr Gly Lys Leu Lys Ser Tyr
            85                  90                  95

Asn Gly Thr Phe Thr Gly Ser Leu Ala Phe Leu Asn Asp Tyr Glu Tyr
            100                 105                 110

Phe Val Pro Asp Asp Ser Leu Tyr Glu Lys Glu Thr Ser Ala Leu Asn
            115                 120                 125

Ser Gln Gly Leu Phe Ala Gly Thr Thr Asp Ala Leu Arg His Gly Ala
            130                 135                 140

Ala Phe Arg Ala Lys Tyr Gly Ser Leu Tyr Lys Gln Asn Ser Thr Leu
145                 150                 155                 160

Pro Val Phe Thr Ser Asn Ser Asn Arg Val Tyr Gln Thr Ser Glu Tyr
                    165                 170                 175

Phe Ala Arg Gly Phe Leu Gly Asp Glu Phe Ser Asp Ala Thr Val His
                    180                 185                 190

Phe Ala Ile Ile Asp Glu Asp Pro Lys Met Gly Val Asn Ser Leu Thr
                    195                 200                 205

Pro Arg Ala Ala Cys Asp Asn Tyr Asn Glu Asp Val Asn Asp Gly Ile
            210                 215                 220

Val Asn Gln Tyr Ser Thr Asp Tyr Leu Asp Glu Ala Leu Lys Arg Phe
225                 230                 235                 240

Gln Ser Ser Asn Pro Gly Leu Asn Leu Thr Ser Glu Asp Val Tyr Gln
                    245                 250                 255

Leu Phe Ala Tyr Cys Ala Tyr Glu Thr Asn Val Lys Gly Ala Ser Pro
                    260                 265                 270

Phe Cys Asp Leu Phe Thr Asn Glu Glu Tyr Ile Gln Tyr Ser Tyr Ser
                    275                 280                 285

Val Asp Leu Ser Asn Tyr Tyr Ser His Gly Ala Gly His Asn Leu Thr
            290                 295                 300

Lys Thr Ile Gly Ser Thr Leu Leu Asn Ala Ser Leu Thr Leu Leu Lys
305                 310                 315                 320

Asp Gly Thr Asn Asp Asn Lys Ile Trp Leu Ser Phe Ser His Asp Thr
                    325                 330                 335

Asp Leu Glu Ile Phe His Ser Ala Leu Gly Ile Val Glu Pro Ala Glu
                    340                 345                 350

Asp Leu Pro Val Asp Tyr Ile Pro Phe Pro Ser Pro Tyr Ile His Ser
                    355                 360                 365
```

```
Gln Ile Val Pro Gln Gly Ala Arg Ile Tyr Thr Glu Lys Tyr Ser Cys
    370                 375                 380

Gly Asn Glu Thr Tyr Val Arg Tyr Ile Leu Asn Asp Ala Val Val Pro
385                 390                 395                 400

Ile Pro Lys Cys Ser Ser Gly Pro Gly Phe Ser Cys Glu Leu Ser Lys
                405                 410                 415

Phe Glu Glu Tyr Ile Asn Lys Arg Leu Arg Asp Val Asp Phe Val Glu
            420                 425                 430

Gln Cys Asp Leu Lys Asp Ala Pro Thr Glu Val Thr Phe Tyr Trp Asp
        435                 440                 445

Tyr Thr Ser Val Asn Tyr Ser Ala Ser Leu Ile Asn Gly
    450                 455                 460
```

<210> SEQ ID NO 2
<211> LENGTH: 461
<212> TYPE: PRT
<213> ORGANISM: Debaryomyces castellii

<400> SEQUENCE: 2

```
Met Val Ser Val Ser Lys Leu Ile Asn Asn Gly Leu Leu Val Gly
1               5                   10                  15

Gln Gly Ala Tyr Gln Asp Leu Ala Ser Pro Gln Gln Ala Ser Val Glu
            20                  25                  30

Gln Tyr Asn Ile Ile Arg Phe Leu Gly Gly Ala Ala Pro Tyr Ile Gln
        35                  40                  45

Asn Lys Gly Phe Gly Ile Ser Thr Asp Ile Pro Asp Gln Cys Thr Leu
    50                  55                  60

Glu Gln Val Gln Leu Phe Ser Arg His Gly Glu Arg Tyr Pro Ser Thr
65                  70                  75                  80

Gly Ser Gly Lys Lys Tyr Lys Ala Val Tyr Glu Lys Leu Met Ser Tyr
                85                  90                  95

Asn Gly Thr Phe Lys Gly Glu Leu Ala Phe Leu Asn Asp Asp Tyr Glu
            100                 105                 110

Tyr Phe Val Pro Asp Ser Val Tyr Leu Glu Lys Glu Thr Ser Pro Lys
        115                 120                 125

Asn Ser Asp Ser Ile Tyr Ala Gly Thr Thr Asp Ala Met Lys His Gly
    130                 135                 140

Ile Ala Phe Arg Thr Lys Tyr Gly Glu Leu Phe Asp Thr Asn Asp Thr
145                 150                 155                 160

Leu Pro Val Phe Thr Ser Asn Ser Gly Arg Val Tyr Gln Thr Ser Gln
                165                 170                 175

Tyr Phe Ala Arg Gly Phe Met Gly Asp Asp Phe Ser Asn Asp Thr Val
            180                 185                 190

Lys Thr Asn Ile Ile Ser Glu Asp Ala Asp Met Gly Ala Asn Ser Leu
        195                 200                 205

Thr Pro Arg Asp Gly Cys Phe Asn Tyr Asn Glu Asn Ala Asn Thr Ala
    210                 215                 220

Ile Val Asp Glu Tyr Thr Thr Glu Tyr Leu Thr Lys Ala Leu Asn Arg
225                 230                 235                 240

Phe Lys Ala Ser Asn Pro Gly Leu Asn Ile Thr Glu Asp Asp Val Ser
                245                 250                 255

Asn Leu Phe Gly Tyr Cys Ala Tyr Glu Leu Asn Val Lys Gly Ala Ser
            260                 265                 270

Pro Met Cys Asp Ile Phe Thr Asn Glu Glu Phe Ile Gln Tyr Ser Tyr
        275                 280                 285
```

-continued

```
Ser Val Asp Leu Asp Asp Tyr Tyr Ser Asn Ser Ala Gly Asn Asn Met
    290                 295                 300

Thr Arg Val Ile Gly Ser Thr Leu Leu Asn Ala Ser Leu Glu Leu Leu
305                 310                 315                 320

Asn His Asp Lys Asn Glu Asn Lys Ile Trp Leu Ser Phe Thr His Asp
                325                 330                 335

Thr Asp Ile Glu Ile Phe His Ser Ala Ile Gly Ile Leu Ile Pro Asp
            340                 345                 350

Glu Asp Leu Pro Val Asp Tyr Thr Pro Phe Pro Ser Pro Tyr Ser His
        355                 360                 365

Val Gly Ile Thr Pro Gln Gly Ala Arg Thr Ile Ile Glu Lys Tyr Ala
    370                 375                 380

Cys Gly Asn Glu Ser Tyr Val Arg Tyr Val Ile Asn Asp Ala Val Ile
385                 390                 395                 400

Pro Ile Lys Lys Cys Ser Ser Gly Pro Gly Phe Ser Cys Asn Leu Asn
                405                 410                 415

Asp Tyr Asn Asp Tyr Val Ala Glu Arg Val Ala Gly Thr Asn Tyr Val
            420                 425                 430

Glu Gln Cys Gly Asn Asn Asn Ala Ser Ala Val Thr Phe Tyr Trp Asp
        435                 440                 445

Tyr Glu Thr Thr Asn Tyr Thr Ala Ser Leu Ile Asn Ser
    450                 455                 460

<210> SEQ ID NO 3
<211> LENGTH: 467
<212> TYPE: PRT
<213> ORGANISM: Aspergillus niger

<400> SEQUENCE: 3

Met Gly Val Ser Ala Val Leu Leu Pro Leu Tyr Leu Leu Ser Gly Val
  1               5                  10                  15

Thr Ser Gly Leu Ala Val Pro Ala Ser Arg Asn Gln Ser Ser Cys Asp
             20                  25                  30

Thr Val Asp Gln Gly Tyr Gln Cys Phe Ser Glu Thr Ser His Leu Trp
         35                  40                  45

Gly Gln Tyr Ala Pro Phe Phe Ser Leu Ala Asn Glu Ser Val Ile Ser
     50                  55                  60

Pro Glu Val Pro Ala Gly Cys Arg Val Thr Phe Ala Gln Val Leu Ser
 65                  70                  75                  80

Arg His Gly Ala Arg Tyr Pro Thr Asp Ser Lys Gly Lys Lys Tyr Ser
                 85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205
```

```
Thr Leu Asp Pro Gly Thr Cys Thr Val Phe Glu Asp Ser Glu Leu Ala
    210                 215                 220
Asp Thr Val Glu Ala Asn Phe Thr Ala Thr Phe Val Pro Ser Ile Arg
225                 230                 235                 240
Gln Arg Leu Glu Asn Asp Leu Ser Gly Val Thr Leu Thr Asp Thr Glu
                245                 250                 255
Val Thr Tyr Leu Met Asp Met Cys Ser Phe Asp Thr Ile Ser Thr Ser
            260                 265                 270
Thr Val Asp Thr Lys Leu Ser Pro Phe Cys Asp Leu Phe Thr His Asp
        275                 280                 285
Glu Trp Ile Asn Tyr Asp Tyr Leu Gln Ser Leu Lys Lys Tyr Tyr Gly
    290                 295                 300
His Gly Ala Gly Asn Pro Leu Gly Pro Thr Gln Gly Val Gly Tyr Ala
305                 310                 315                 320
Asn Glu Leu Ile Ala Arg Leu Thr His Ser Pro Val His Asp Asp Thr
                325                 330                 335
Ser Ser Asn His Thr Leu Asp Ser Ser Pro Ala Thr Phe Pro Leu Asn
            340                 345                 350
Ser Thr Leu Tyr Ala Asp Phe Ser His Asp Asn Gly Ile Ile Ser Ile
        355                 360                 365
Leu Phe Ala Leu Gly Leu Tyr Asn Gly Thr Lys Pro Leu Ser Thr Thr
    370                 375                 380
Thr Val Glu Asn Ile Thr Gln Thr Asp Gly Phe Ser Ser Ala Trp Thr
385                 390                 395                 400
Val Pro Phe Ala Ser Arg Leu Tyr Val Glu Met Met Gln Cys Gln Ala
                405                 410                 415
Glu Gln Glu Pro Leu Val Arg Val Leu Val Asn Asp Arg Val Val Pro
            420                 425                 430
Leu His Gly Cys Pro Val Asp Ala Leu Gly Arg Cys Thr Arg Asp Ser
        435                 440                 445
Phe Val Arg Gly Leu Ser Phe Ala Arg Ser Gly Gly Asp Trp Ala Glu
    450                 455                 460
Cys Phe Ala
465

<210> SEQ ID NO 4
<211> LENGTH: 540
<212> TYPE: PRT
<213> ORGANISM: Penicillium funiculosum

<400> SEQUENCE: 4

Met Leu Lys Leu Tyr Val Ala Ala Cys Leu Val Val Ala Gly Val Ser
  1               5                  10                  15
Ile Pro Thr Asp Pro Thr Val Thr Gln Val Pro Asp Tyr Phe Gln Thr
             20                  25                  30
Ser Tyr Gly Pro Tyr Ala Gly Ala Thr Lys Ala Gly Ala Pro Phe
         35                  40                  45
Leu Ala Gln Thr Asn Pro Ile Tyr Ser Gln Pro Thr Tyr Val Ala Asn
     50                  55                  60
Thr Pro Leu Val Thr Thr Leu Pro Ile Ser Gly Glu Pro His Asp Gly
65                  70                  75                  80
Asn Ile Phe Gly Trp Met Gly Thr Leu Ser Pro Tyr Gln Pro Ser Pro
                 85                  90                  95
Asp Gly Phe Gly Val Asp Glu Tyr Pro Leu Pro Pro Gly Ala Asn Ile
            100                 105                 110
```

```
Thr Gln Ile His Met Val His Arg His Gly Ser Arg Tyr Pro Thr Ser
        115                 120                 125
Asn Ser Ala Ile Ser Asp Trp Ala Lys Lys Ile Met Gln Tyr Arg Ser
130                 135                 140
Asn Gly Thr Val Phe Ser Gly Glu Leu Glu Phe Leu Asn Ala Trp Asn
145                 150                 155                 160
Tyr Gln Leu Gly Gln Ala Glu Leu Thr Ala Arg Gly Arg Gln Glu Leu
                165                 170                 175
Phe Asp Ser Gly Ile Leu His Trp Phe Asn Tyr Gly Lys Leu Tyr Asp
            180                 185                 190
Pro Ala Ser Lys Ile Ile Ala Arg Thr Thr Met Val Arg Met Leu
        195                 200                 205
Gln Ser Ala Glu Asn Phe Leu Asn Gly Phe Phe Gly Pro Asn Trp Thr
        210                 215                 220
Asn Asn Ala Thr Leu Glu Val Ile Ile Glu Ser Thr Gly Phe Asn Asn
225                 230                 235                 240
Ser Leu Ala Gly Asn Asp Met Cys Arg Asn Ala Lys Asn Thr Ser Gly
                245                 250                 255
Gly Asp Ala Val Asn Glu Trp Thr Ala Leu Tyr Leu Gln Lys Ala Thr
                260                 265                 270
Asn Arg Phe Arg Ser Glu Ile Ser Gly Ser Leu Asn Trp Thr Val Asp
            275                 280                 285
Asp Thr Tyr Asn Ala Gln Ser Met Cys Pro Tyr Glu Thr Val Ala Leu
        290                 295                 300
Gly Tyr Ser Pro Phe Cys Thr Leu Phe Ser Trp Glu Glu Trp Gln Gly
305                 310                 315                 320
Phe Gln Tyr Val Asn Asp Leu Asn Leu Tyr Gly Asn Tyr Gly Met Gly
                325                 330                 335
Ser Pro Val Gly Arg Ala Ile Gly Leu Gly Phe Val Glu Glu Leu Ile
                340                 345                 350
Ala Arg Leu Gln Gly Gln Ile Pro Asn Pro Pro Glu Asp Ser Ile Gly
            355                 360                 365
Phe Asn Gln Ser Leu Asp Asp Ser Ala Ala Thr Phe Pro Leu Asn Gln
        370                 375                 380
Thr Ile Tyr Phe Asp Phe Ser His Asp Asn Glu Met Phe Ser Met Leu
385                 390                 395                 400
Thr Ala Leu Gly Leu Thr Gln Phe Gly Asp Tyr Leu Ser Pro Thr Lys
                405                 410                 415
Pro Ser Ala Asp Arg Ser Leu Ile Gly Ser His Ile Val Pro Phe Ser
                420                 425                 430
Ala Thr Phe Val Phe Glu Ile Ile Lys Ala Pro Gly Leu Val Arg Glu
            435                 440                 445
Asn Arg Ser Lys Tyr Cys Gly Glu Ser Val Tyr Glu Asn Thr Ser Glu
450                 455                 460
Glu Thr Thr Tyr Ile His Leu Val Ile Asn Gln Arg Thr Val Pro Leu
465                 470                 475                 480
Gly Gln Ser Ile Ser Ala Cys Gly Gln Arg Asp Gly Trp Cys Glu
                485                 490                 495
Ile Ser Ala Phe Ile Gln Ala Gln Lys Glu Asn Ile Val Lys Ala Asn
                500                 505                 510
Tyr Glu Glu Ser Cys Phe Gly Asn Trp Ser Ile Pro Ala Tyr Gly Glu
            515                 520                 525
Ile Arg Asp Gly Ala Ile Pro Lys Asn Ala Thr Ser
```

<210> SEQ ID NO 5
<211> LENGTH: 439
<212> TYPE: PRT
<213> ORGANISM: Peniophora lycii

<400> SEQUENCE: 5

```
Met Val Ser Ser Ala Phe Ala Pro Ser Ile Leu Leu Ser Leu Met Ser
  1               5                  10                  15

Ser Leu Ala Leu Ser Thr Gln Phe Ser Phe Val Ala Ala Gln Leu Pro
             20                  25                  30

Ile Pro Ala Gln Asn Thr Ser Asn Trp Gly Pro Tyr Asp Pro Phe Phe
         35                  40                  45

Pro Val Glu Pro Tyr Ala Ala Pro Pro Glu Gly Cys Thr Val Thr Gln
     50                  55                  60

Val Asn Leu Ile Gln Arg His Gly Ala Arg Trp Pro Thr Ser Gly Ala
 65                  70                  75                  80

Arg Ser Arg Gln Val Ala Ala Val Ala Lys Ile Gln Met Ala Arg Pro
                 85                  90                  95

Phe Thr Asp Pro Lys Tyr Glu Phe Leu Asn Asp Phe Val Tyr Lys Phe
            100                 105                 110

Gly Val Ala Asp Leu Leu Pro Phe Gly Ala Asn Gln Ser His Gln Thr
        115                 120                 125

Gly Thr Asp Met Tyr Thr Arg Tyr Ser Thr Leu Phe Glu Gly Gly Asp
    130                 135                 140

Val Pro Phe Val Arg Ala Ala Gly Asp Gln Arg Val Val Asp Ser Ser
145                 150                 155                 160

Thr Asn Trp Thr Ala Gly Phe Gly Asp Ala Ser Gly Glu Thr Val Leu
                165                 170                 175

Pro Thr Leu Gln Val Val Leu Gln Glu Glu Gly Asn Cys Thr Leu Cys
            180                 185                 190

Asn Asn Met Cys Pro Asn Glu Val Asp Gly Asp Glu Ser Thr Thr Trp
        195                 200                 205

Leu Gly Val Phe Ala Pro Asn Ile Thr Ala Arg Leu Asn Ala Ala Ala
    210                 215                 220

Pro Ser Ala Asn Leu Ser Asp Ser Asp Ala Leu Thr Leu Met Asp Met
225                 230                 235                 240

Cys Pro Phe Asp Thr Leu Ser Ser Gly Asn Ala Ser Pro Phe Cys Asp
                245                 250                 255

Leu Phe Thr Ala Glu Glu Tyr Val Ser Tyr Glu Tyr Tyr Tyr Asp Leu
            260                 265                 270

Asp Lys Tyr Tyr Gly Thr Gly Pro Gly Asn Ala Leu Gly Pro Val Gln
        275                 280                 285

Gly Val Gly Tyr Val Asn Glu Leu Leu Ala Arg Leu Thr Gly Gln Ala
    290                 295                 300

Val Arg Asp Glu Thr Gln Thr Asn Arg Thr Leu Asp Ser Asp Pro Ala
305                 310                 315                 320

Thr Phe Pro Leu Asn Arg Thr Phe Tyr Ala Asp Phe Ser His Asp Asn
                325                 330                 335

Thr Met Val Pro Ile Phe Ala Ala Leu Gly Leu Phe Asn Ala Thr Ala
            340                 345                 350

Leu Asp Pro Leu Lys Pro Asp Glu Asn Arg Leu Trp Val Asp Ser Lys
        355                 360                 365

Leu Val Pro Phe Ser Gly His Met Thr Val Glu Lys Leu Ala Cys Ser
```

```
                    370                 375                 380
Gly Lys Glu Ala Val Arg Val Leu Val Asn Asp Ala Val Gln Pro Leu
385                 390                 395                 400

Glu Phe Cys Gly Gly Val Asp Gly Val Cys Glu Leu Ser Ala Phe Val
                405                 410                 415

Glu Ser Gln Thr Tyr Ala Arg Glu Asn Gly Gln Gly Asp Phe Ala Lys
            420                 425                 430

Cys Gly Phe Val Pro Ser Glu
            435

<210> SEQ ID NO 6
<211> LENGTH: 1623
<212> TYPE: DNA
<213> ORGANISM: Triticum aestivum
<220> FEATURE:
<221> NAME/KEY: CDS
<222> LOCATION: (1)..(1623)

<400> SEQUENCE: 6 atg tgg atg tgg agg ggg tcg ctg ccg ctg ctt ctg ctc gcc gcg gcg        48
Met Trp Met Trp Arg Gly Ser Leu Pro Leu Leu Leu Leu Ala Ala Ala
 1               5                  10                  15 gtg gcg gcg gcg gct gag ccg gcg tcg acg ctg gag gga ccg tcg cgg        96
Val Ala Ala Ala Ala Glu Pro Ala Ser Thr Leu Glu Gly Pro Ser Arg
                20                  25                  30 ccg gtg acg gtg ccg ctg cgg gaa gac agg ggc cac gcg gtg gac ctg       144
Pro Val Thr Val Pro Leu Arg Glu Asp Arg Gly His Ala Val Asp Leu
            35                  40                  45 ccg gac acg gac ccc cgg gtg cag cgc cgg gtc aca ggc tgg gct ccc       192
Pro Asp Thr Asp Pro Arg Val Gln Arg Arg Val Thr Gly Trp Ala Pro
    50                  55                  60 gag cag atc gcc gtc gcg ctc tcc gcc gct ccc acc tcc gcc tgg gtc       240
Glu Gln Ile Ala Val Ala Leu Ser Ala Ala Pro Thr Ser Ala Trp Val
65                  70                  75                  80 tcc tgg atc aca ggg gat ttc cag atg ggc ggc gcc gtc aag ccg ctg       288
Ser Trp Ile Thr Gly Asp Phe Gln Met Gly Gly Ala Val Lys Pro Leu
                85                  90                  95 gac ccc ggc acg gtc ggc agc gtc gtg cgc tac ggc ctc gcc gcc gat       336
Asp Pro Gly Thr Val Gly Ser Val Val Arg Tyr Gly Leu Ala Ala Asp
            100                 105                 110 tct ttg gtc cgc gag gcc acc ggc gac gcg ctc gtg tac agc cag ctc       384
Ser Leu Val Arg Glu Ala Thr Gly Asp Ala Leu Val Tyr Ser Gln Leu
    115                 120                 125 tac ccc ttc gag ggc ctc cag aac tac acc tcc ggc atc atc cac cac       432
Tyr Pro Phe Glu Gly Leu Gln Asn Tyr Thr Ser Gly Ile Ile His His
130                 135                 140 gtc cgc ctc caa ggg ctt gag cct ggg acg aag tac tac tac cag tgc       480
Val Arg Leu Gln Gly Leu Glu Pro Gly Thr Lys Tyr Tyr Tyr Gln Cys
145                 150                 155                 160 ggc gac ccg gcc atc ccg ggg gcg atg agc gcc gtc cac gcg ttc cgg       528
Gly Asp Pro Ala Ile Pro Gly Ala Met Ser Ala Val His Ala Phe Arg
                165                 170                 175 acg atg ccg gcg gtc ggg ccg cgg agc tac ccg ggg agg atc gcc gtg       576
Thr Met Pro Ala Val Gly Pro Arg Ser Tyr Pro Gly Arg Ile Ala Val
            180                 185                 190 gtg ggg gac ctc ggg ctc acg tac aac acc acc tcg acc gtg gac cac       624
Val Gly Asp Leu Gly Leu Thr Tyr Asn Thr Thr Ser Thr Val Asp His
    195                 200                 205 atg gcg agc aac cgg ccg gac ctg gtg ctc ctc gtc ggc gac gtg tgc       672
Met Ala Ser Asn Arg Pro Asp Leu Val Leu Leu Val Gly Asp Val Cys
210                 215                 220
```

|  |  |
|---|---:|
| tac gcc aac atg tac ctc acc aac ggc acc gga gcg gac tgc tac tcg<br>Tyr Ala Asn Met Tyr Leu Thr Asn Gly Thr Gly Ala Asp Cys Tyr Ser<br>225                         230                         235                    240 | 720 |
| tgc gcg ttc ggc aag tcg acg ccc atc cac gag acg tac cag ccg cgc<br>Cys Ala Phe Gly Lys Ser Thr Pro Ile His Glu Thr Tyr Gln Pro Arg<br>                       245                         250                        255 | 768 |
| tgg gac tac tgg gga agg tac atg gag gcg gtg acg tcg ggg acg ccg<br>Trp Asp Tyr Trp Gly Arg Tyr Met Glu Ala Val Thr Ser Gly Thr Pro<br>               260                         265                        270 | 816 |
| atg atg gtg gtg gaa ggg aac cat gag ata gag gag cag atc ggg aac<br>Met Met Val Val Glu Gly Asn His Glu Ile Glu Glu Gln Ile Gly Asn<br>      275                       280                         285 | 864 |
| aag acg ttc gcg gcc tac cgc tcc cgg ttc gcg ttc ccg tcg acg gag<br>Lys Thr Phe Ala Ala Tyr Arg Ser Arg Phe Ala Phe Pro Ser Thr Glu<br>290                         295                         300 | 912 |
| agc ggg tcc ttc tcc ccc ttc tac tac tcg ttc gac gcc ggc ggg atc<br>Ser Gly Ser Phe Ser Pro Phe Tyr Tyr Ser Phe Asp Ala Gly Gly Ile<br>305                       310                         315                   320 | 960 |
| cat ttc ctc atg ctc ggc gcc tac gcc gac tac ggc agg tca ggg gag<br>His Phe Leu Met Leu Gly Ala Tyr Ala Asp Tyr Gly Arg Ser Gly Glu<br>                       325                         330                        335 | 1008 |
| cag tac aga tgg ctg gag aag gac ctg gcg aag gtg gac agg tcg gtg<br>Gln Tyr Arg Trp Leu Glu Lys Asp Leu Ala Lys Val Asp Arg Ser Val<br>               340                         345                        350 | 1056 |
| acg ccg tgg ctg gtc gcc ggc tgg cac gcg cca tgg tac acc acc tac<br>Thr Pro Trp Leu Val Ala Gly Trp His Ala Pro Trp Tyr Thr Thr Tyr<br>      355                       360                         365 | 1104 |
| aag gct cac tac agg gag gtg gag tgc atg aga gtg gcc atg gag gag<br>Lys Ala His Tyr Arg Glu Val Glu Cys Met Arg Val Ala Met Glu Glu<br>370                         375                         380 | 1152 |
| ctg ctc tac tcc cac ggc ctc gac atc gcc ttc acc ggc cat gtg cac<br>Leu Leu Tyr Ser His Gly Leu Asp Ile Ala Phe Thr Gly His Val His<br>385                         390                         395                   400 | 1200 |
| gcg tat gag cgc tcc aac cgg gtg ttc aac tac acg ctg gac ccg tgc<br>Ala Tyr Glu Arg Ser Asn Arg Val Phe Asn Tyr Thr Leu Asp Pro Cys<br>                       405                         410                        415 | 1248 |
| ggc gcc gtg cac atc tcg gtg ggc gac ggc ggg aac cgc gag aag atg<br>Gly Ala Val His Ile Ser Val Gly Asp Gly Gly Asn Arg Glu Lys Met<br>               420                         425                        430 | 1296 |
| gcc acc acc cac gcc gac gag cca ggg cac tgc ccg gac ccg cgg ccc<br>Ala Thr Thr His Ala Asp Glu Pro Gly His Cys Pro Asp Pro Arg Pro<br>      435                       440                         445 | 1344 |
| aag ccc aac gcc ttc atc ggc ggc ttc tgc gcc ttt aac ttc acg tcc<br>Lys Pro Asn Ala Phe Ile Gly Gly Phe Cys Ala Phe Asn Phe Thr Ser<br>450                         455                         460 | 1392 |
| ggc ccg gcc gcc ggc agg ttc tgc tgg gac cgg cag ccg gac tac agc<br>Gly Pro Ala Ala Gly Arg Phe Cys Trp Asp Arg Gln Pro Asp Tyr Ser<br>465                       470                         475                   480 | 1440 |
| gcc tac cgg gag agc agc ttc ggc cac ggc atc ctc gag gtg aag aac<br>Ala Tyr Arg Glu Ser Ser Phe Gly His Gly Ile Leu Glu Val Lys Asn<br>                       485                         490                        495 | 1488 |
| gag acg cac gct ctg tgg aga tgg cac agg aac cag gac atg tac ggg<br>Glu Thr His Ala Leu Trp Arg Trp His Arg Asn Gln Asp Met Tyr Gly<br>               500                         505                        510 | 1536 |
| agc gcc gga gat gag att tac att gtc cgg gag ccg cac agg tgc ttg<br>Ser Ala Gly Asp Glu Ile Tyr Ile Val Arg Glu Pro His Arg Cys Leu<br>      515                       520                         525 | 1584 |
| cac aaa cac aac tgg acc agg ccc gca cac ggt ccg taa<br>His Lys His Asn Trp Thr Arg Pro Ala His Gly Pro<br>530                         535                         540 | 1623 |

<210> SEQ ID NO 7
<211> LENGTH: 540
<212> TYPE: PRT
<213> ORGANISM: Triticum aestivum

<400> SEQUENCE: 7

```
Met Trp Met Trp Arg Gly Ser Leu Pro Leu Leu Leu Ala Ala Ala
 1               5                  10                  15

Val Ala Ala Ala Glu Pro Ala Ser Thr Leu Glu Gly Pro Ser Arg
                20                  25                  30

Pro Val Thr Val Pro Leu Arg Glu Asp Arg Gly His Ala Val Asp Leu
            35                  40                  45

Pro Asp Thr Asp Pro Arg Val Gln Arg Arg Val Thr Gly Trp Ala Pro
     50                  55                  60

Glu Gln Ile Ala Val Ala Leu Ser Ala Ala Pro Thr Ser Ala Trp Val
 65                  70                  75                  80

Ser Trp Ile Thr Gly Asp Phe Gln Met Gly Gly Ala Val Lys Pro Leu
                 85                  90                  95

Asp Pro Gly Thr Val Gly Ser Val Val Arg Tyr Gly Leu Ala Ala Asp
            100                 105                 110

Ser Leu Val Arg Glu Ala Thr Gly Asp Ala Leu Val Tyr Ser Gln Leu
        115                 120                 125

Tyr Pro Phe Glu Gly Leu Gln Asn Tyr Thr Ser Gly Ile Ile His His
    130                 135                 140

Val Arg Leu Gln Gly Leu Glu Pro Gly Thr Lys Tyr Tyr Tyr Gln Cys
145                 150                 155                 160

Gly Asp Pro Ala Ile Pro Gly Ala Met Ser Ala Val His Ala Phe Arg
                165                 170                 175

Thr Met Pro Ala Val Gly Pro Arg Ser Tyr Pro Gly Arg Ile Ala Val
            180                 185                 190

Val Gly Asp Leu Gly Leu Thr Tyr Asn Thr Thr Ser Thr Val Asp His
        195                 200                 205

Met Ala Ser Asn Arg Pro Asp Leu Val Leu Leu Val Gly Asp Val Cys
    210                 215                 220

Tyr Ala Asn Met Tyr Leu Thr Asn Gly Thr Gly Ala Asp Cys Tyr Ser
225                 230                 235                 240

Cys Ala Phe Gly Lys Ser Thr Pro Ile His Glu Thr Tyr Gln Pro Arg
                245                 250                 255

Trp Asp Tyr Trp Gly Arg Tyr Met Glu Ala Val Thr Ser Gly Thr Pro
            260                 265                 270

Met Met Val Val Glu Gly Asn His Glu Ile Glu Glu Gln Ile Gly Asn
        275                 280                 285

Lys Thr Phe Ala Ala Tyr Arg Ser Arg Phe Ala Phe Pro Ser Thr Glu
    290                 295                 300

Ser Gly Ser Phe Ser Pro Phe Tyr Tyr Ser Phe Asp Ala Gly Gly Ile
305                 310                 315                 320

His Phe Leu Met Leu Gly Ala Tyr Ala Asp Tyr Gly Arg Ser Gly Glu
                325                 330                 335

Gln Tyr Arg Trp Leu Glu Lys Asp Leu Ala Lys Val Asp Arg Ser Val
            340                 345                 350

Thr Pro Trp Leu Val Ala Gly Trp His Ala Pro Trp Tyr Thr Thr Tyr
        355                 360                 365

Lys Ala His Tyr Arg Glu Val Glu Cys Met Arg Val Ala Met Glu Glu
    370                 375                 380
```

```
Leu Leu Tyr Ser His Gly Leu Asp Ile Ala Phe Thr Gly His Val His
385             390             395             400

Ala Tyr Glu Arg Ser Asn Arg Val Phe Asn Tyr Thr Leu Asp Pro Cys
            405             410             415

Gly Ala Val His Ile Ser Val Gly Asp Gly Gly Asn Arg Glu Lys Met
            420             425             430

Ala Thr Thr His Ala Asp Glu Pro Gly His Cys Pro Asp Pro Arg Pro
            435             440             445

Lys Pro Asn Ala Phe Ile Gly Gly Phe Cys Ala Phe Asn Phe Thr Ser
        450             455             460

Gly Pro Ala Ala Gly Arg Phe Cys Trp Asp Arg Gln Pro Asp Tyr Ser
465             470             475             480

Ala Tyr Arg Glu Ser Ser Phe Gly His Gly Ile Leu Glu Val Lys Asn
            485             490             495

Glu Thr His Ala Leu Trp Arg Trp His Arg Asn Gln Asp Met Tyr Gly
            500             505             510

Ser Ala Gly Asp Glu Ile Tyr Ile Val Arg Glu Pro His Arg Cys Leu
            515             520             525

His Lys His Asn Trp Thr Arg Pro Ala His Gly Pro
530             535             540
```

SYNERGETIC EFFECT OF THE PHYTASE COMBINATION ON THE HYDROLYSIS OF PHYTIC ACID

Figure 1:
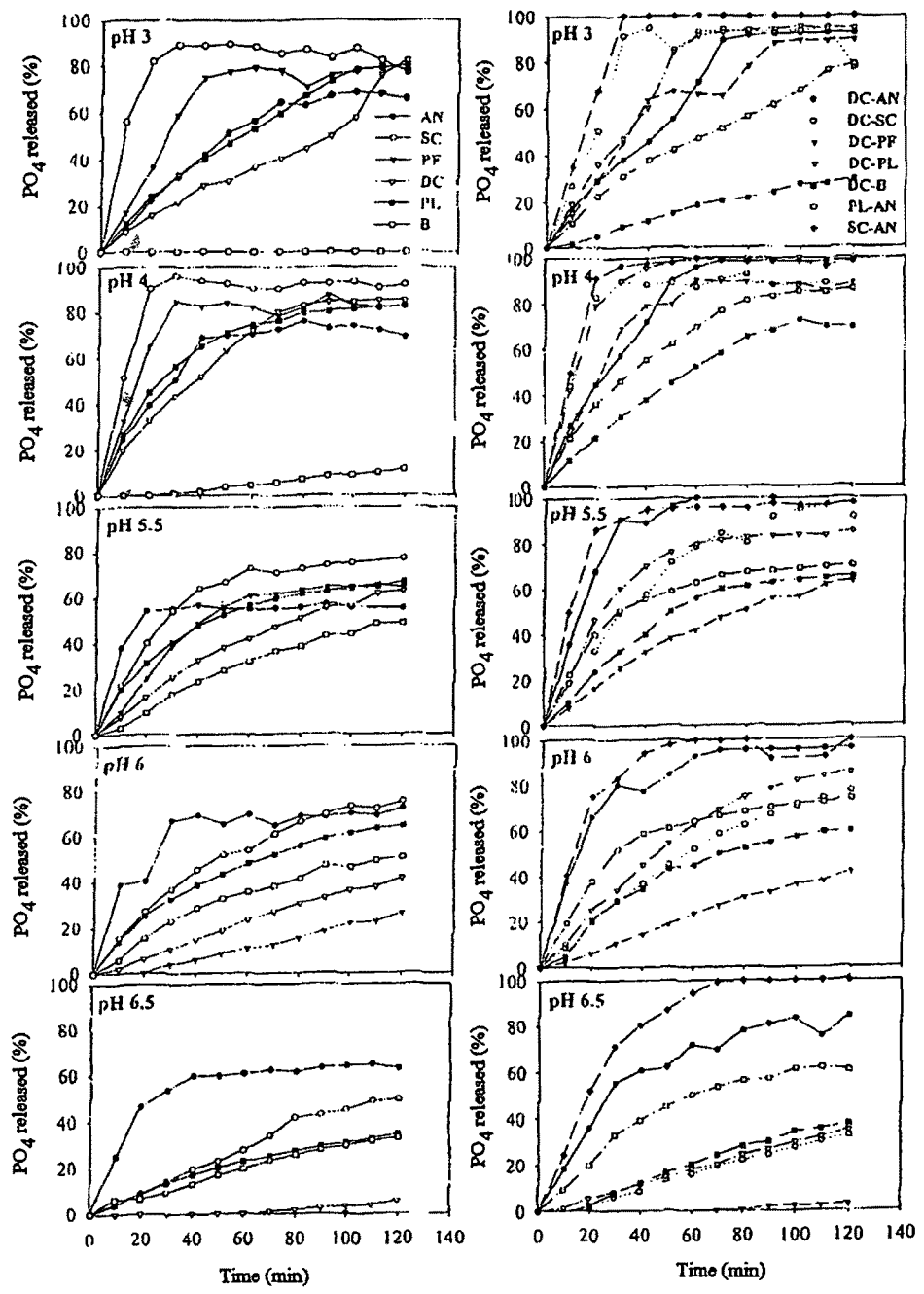

The invention relates to the synergistic effect of the combination of phytases on phytic acid hydrolysis.

Phytic acid salts (myo-inositol hexakisphosphate) or phytates (myo-inositol hexakis dihydrogen phosphate) are the major storage form of phosphorus in cereals, leguminous plants and oil-yielding plants. They thus constitute the main source of phosphorus in plant-based animal feeds, the main components in the diets of monogastric animals (poultry and pigs). However, the bioavailability of this phosphorus in feeds is limited for these animals. This is because they do not possess the intestinal enzymes that degrade phytates in sufficient amount to allow phytate hydrolysis and thus provide the amounts of inorganic phosphate that they require. In addition, phytic acid is an antinutritional factor, which forms complexes with proteins and ions ($Fe^{3+}$, $Ca^{2+}$, $Zn^{2+}$, $Mg^{2+}$) and thus decreases the availability of these elements.

The feed intake of poultry and pigs must therefore be supplemented with inorganic phosphate, while the phosphorus of the phytates is excreted and contributes to the eutrophication of surface water in areas where there is intensive rearing of monogastric animals.

Phytases (myo-inositol hexakisphosphate 3- and 6-phosphohydrolases EC 3.1.3.8 and 3.1.3.26) are part of the family of histidine acid phosphatases. Phytases are hexakisphosphohydrolases which hydrolyse the phosphoester bonds in phytic acid or phytate. Thus, they catalyse the hydrolysis of myo-inositol hexakisphosphate (phytic acid, $InsP_6$) to inorganic monophosphates and to myo-inositol phosphates with a lower degree of phosphorylation ($InsP_5$ to $InsP_1$) and to free myo-inositol in certain cases.

Two classes of phytase exist, differentiated only by the position of the first phosphate hydrolysed. 3-Phytases (EC 3.1.3.8) hydrolyse the phosphate in the 3-position and 6-phytases (EC 3.1.3.26) hydrolyse the phosphate in the 6-position.

These enzymes, used as an additive in animal nutrition, make it possible, firstly, to increase the availability of the phytic phosphorus and, secondly, to improve the digestibility of the feeds. In addition, the release of phytic phosphate considerably decreases the costs due to supplementation with phosphate, and also the pollution caused by an excess of excreted phosphates.

Phytases are produced by a large variety of organisms: plants, animals and especially microorganisms. These phytases have very different biochemical characteristics, in particular their activity as a function of pH and their temperature stability. In addition, these enzymes exhibit differences in terms: (a) of their effectiveness in hydrolysing all the phosphates, (b) of their stereospecificity and (c) of their affinity with respect to inositol phosphates.

Among phytase-producing microorganisms, mention will in particular be made of: fungi of the genera *Aspergillus, Penicillium, Mucor* and *Rhizopus*, bacteria: *Pseudomonas* sp., *Klebsiella* sp., *Escherichia coli, Enterobacter* sp., *Bacillus subtilis* and yeast: *Saccharomyces cerevisiae, Candida tropicalis, Torulopsis candida, Debaryomyces castellii, Debaryomyces occidentalis* (synonym *Schwanniomyces castellii*), *Kluyveromyces fragilis*.

Numerous microorganism phytases have already been studied and used in various agro-industrial applications. The effectiveness of these enzymes in the feed and in the course of digestion in the animal depend on their ability to maintain their potential, irrespective of the various conditions encountered during the feed preparation steps and in the digestive tract. Preparation of the feeds requires thermoresistant enzymes, whereas the pH values range, for example, between 5.02, 2.75, 6.28, 6.63 and 5.98 during passage through the various crop, stomach, duodenum, jejunum and ileum compartments of poultry.

Most of the phytases described to date only partially hydrolyse phytic acid and some with very slow kinetics. Thus, numerous phytases hydrolyse only 5 phosphate bonds of phytic acid, i.e. 83% of the potential phosphorus.

To date, among yeast, only the phytase of the yeast *Schwanniomyces occidentalis* has been described as being capable of hydrolysing all the phosphate bonds of phytate (EP 0 699 762 and Segueilha L., Lambrechts C., Boze H., Moulin G., Galzy P., (1992) Purification and properties of a phytase from *Schwanniomyces castellii*, J. Ferm. Bioeng., 74, 7-11).

Under experimental conditions, complete hydrolysis of phytate or of phytic acid is not, however, obtained.

In order to obtain a more effective hydrolysis of phytic acid, it has thus been proposed to combine various phytases.

WO 98/30681 describes the combination of phytases having various stereospecificities, and in particular the combination of 3-phytase and of 6-phytase. This document describes in particular the combination of a *Peniophora lycii* 6-phytase and an *Aspergillus niger* 3-phytase (phytase Novo™).

U.S. Pat. No. 6,183,740 also describes the combination of phytases of various specificities and also the combination with other acid phosphatases.

Complete hydrolysis of phytic acid to phosphate and to inositol is not, however, observed.

The problem that the present invention is intended to solve consists in improving the rate and the effectiveness of hydrolysis of phytic acid in order to obtain complete hydrolysis of phytic acid in various agro-industrial applications.

This problem is solved by the compositions and the methods of the present invention in which at least two specific phytases are combined. Advantageously, the compositions of the present invention allow complete hydrolysis of all the phosphate groups of phytic acid by virtue of the synergistic effect observed. Advantageously, the compositions of the present invention are active in a wide pH range suitable for agro-industrial applications of phytases, and in particular for applications in the animal nutrition field. Another advantage of the present invention is that the phytases used are thermostable.

Sequence Description
SEQ ID No. 1: *Schwanniomyces castellii* phytase.
SEQ ID No. 2: *Debaryomyces castellii* phytase.
SEQ ID No. 3: *Aspergillus niger* phytase.
SEQ ID No. 4: *Penicillium funiculosum* phytase.
SEQ ID No. 5: *Peniophora lycii* phytase.
SEQ ID No. 6: Sequence encoding wheat phytase.
SEQ ID No. 7: Wheat (*Triticum aestivum*) phytase.

DESCRIPTION OF THE INVENTION

A subject of the invention is a composition combining at least two phytases for the hydrolysis of phytic acid (myo-inositol 1,2,3,4,5,6-hexakisphosphate), comprising:
- a first phytase exhibiting at least 80% identity with the phytase of SEQ ID No. 1 or exhibiting at least 80% identity with the phytase of SEQ ID No. 2;
- a second phytase exhibiting at least 80% identity with the phytase of SEQ ID No. 3.

Preferably, the first phytase is a 3-phytase which catalyses the hydrolysis of the six phosphate bonds of phytic acid.

Preferably, the first phytase has an optimum temperature of between 55° C. and 80° C. and an optimum pH of between pH 3.5 and pH 5.

In a preferred embodiment, the first phytase is a phytase of the yeast *Schwanniomyces castellii* or a phytase of the yeast *Debaryomyces castellii*.

In another preferred embodiment, the first phytase is the phytase of SEQ ID No. 1 or the phytase of SEQ ID No. 2.

Preferably, the second phytase is a 3-phytase which catalyses the hydrolysis of at least five phosphate bonds of phytic acid.

Preferably, the second phytase has an optimum temperature of between 50° C. and 60° C. and an optimum pH of between pH 2 and pH 6.

In a preferred embodiment, the second phytase is an *Aspergillus niger* phytase.

In another preferred embodiment, the second phytase is the phytase of SEQ ID No. 3.

Preferably, the compositions according to the invention consist of a nutritional additive for animals or of an animal feed.

A subject of the invention is also the use of a composition according to the invention, for the manufacture of a nutritional additive for animals or of an animal feed.

A subject of the invention is also the use of a composition according to the invention, for increasing the availability of phytic phosphorus and improving the digestibility of animal feeds.

The present invention also relates to a method of hydrolysis of phytic acid (myo-inositol 1,2,3,4,5,6-hexakisphosphate) to inorganic monophosphates, to myo-inositols with a lower degree of phosphorylation and to free myo-inositol, comprising the following steps:

a first phytase exhibiting at least 80% identity with the phytase of SEQ ID No. 1 or exhibiting at least 80% identity with the phytase of SEQ ID No. 2 is provided;

a second phytase exhibiting at least 80% identity with the phytase of SEQ ID No. 3 is provided;

the phytic acid is simultaneously brought into contact with the first phytase and the second phytase.

Preferably, the first phytase is a 3-phytase which catalyses the hydrolysis of the six phosphate bonds of phytic acid.

Preferably, the first phytase has an optimum temperature of between 55° C. and 80° C. and an optimum pH of between pH 3.5 and pH 5.

In a preferred embodiment, the first phytase is a phytase of the yeast *Schwanniomyces castellii* or a phytase of the yeast *Debaryomyces castellii*.

In a particularly advantageous embodiment, the first phytase is the phytase of SEQ ID No. 1 or the phytase of SEQ ID No. 2.

Preferably, the second phytase is a 3-phytase which catalyses the hydrolysis of at least five phosphate bonds of phytic acid.

Preferably, the second phytase has an optimum temperature of between 50° C. and 60° C. and an optimum pH of between pH 2 and pH 6.

In an advantageous embodiment, the second phytase is an *Aspergillus niger* phytase.

In a particularly advantageous embodiment, the second phytase is the phytase of SEQ ID No. 3.

A subject of the invention is also a kit or assembly for feeding animals, comprising:

the *Schwanniomyces castellii* phytase of SEQ ID No. 1 or the *Debaryomyces castellii* phytase of SEQ ID No. 2;

the *Aspergillus niger* phytase of SEQ ID No. 3.

The compositions according to the invention combine a first phytase exhibiting at least 80% identity with the phytase of SEQ ID No. 1 or exhibiting at least 80% identity with the phytase of SEQ ID No. 2; and a second phytase exhibiting at least 80% identity with the phytase of SEQ ID No. 3.

Surprisingly, this specific combination of phytases makes it possible to obtain a synergistic effect on the hydrolysis of phytic acid. The compositions according to the invention thus catalyse a rapid and complete hydrolysis of phytic acid in a wide pH range.

The term "phytase" is intended to mean myo-inositol hexakisphosphate phosphohydrolases (EC 3.1.3.8 and 3.1.3.26). These enzymes catalyse the hydrolysis of myo-inositol 1,2,3,4,5,6-hexakisphosphate (phytic acid, $InsP_6$) to inorganic monophosphates and to myo-inositol phosphate with a lower degree of phosphorylation ($InsP_5$ to $InsP_1$) and to free myo-inositol for certain phytases.

The compositions according to the invention comprise a first phytase exhibiting at least 80% identity with the phytase of SEQ ID No. 1 or exhibiting at least 80% identity with the phytase of SEQ ID No. 2.

The phytase of SEQ ID No. 1 is a phytase of the yeast *Schwanniomyces castellii*, while the phytase of SEQ ID No. 2 is a phytase of the yeast *Debaryomyces castellii*.

These phytases have very similar catalytic properties and are therefore interchangeable in the phytase combinations according to the invention.

Preferably, the first phytase exhibits at least 80%, 90%, 95%, 98%, and preferably at least 99%, of amino acids that are identical with the phytase of SEQ ID No. 1 or exhibit at least 80%, 90%, 95%, 98%, and preferably at least 99%, of amino acids identical with the phytase of SEQ ID No. 2.

Preferably, the first phytase has the same properties and in particular the same catalytic properties as the phytases of SEQ ID No. 1 and of SEQ ID No. 2. Preferably, the first phytase is isolated from other strains of *Schwanniomyces castellii* or of *Debaryomyces castellii* or from other yeast. Alternatively, the first phytase can be obtained by site-directed mutagenesis techniques, for example.

The expression "amino acids that are identical" is intended to mean amino acids which do not vary between two sequences. The first phytase can exhibit a deletion, an addition or a substitution of at least one amino acid with respect to the phytases of SEQ ID No. 1 or of SEQ ID No. 2.

The phytases of SEQ ID No. 1 and of SEQ ID No. 2 have common catalytic properties. According to the invention, the first phytase used in the compositions and the methods according to the invention exhibit a degree of identity with the phytase of SEQ ID No. 1 or of SEQ ID No. 2 and conserve these common catalytic properties.

Preferably, the first phytase has 3-phytase activity. Preferably, the first phytase catalyses the hydrolysis of the six phosphate bonds of phytic acid.

The 3-phytases (EC 3.1.3.8) hydrolyse firstly the phosphate in the 3-position.

A phytase capable of hydrolysing all the phosphate bonds of phytic acid (1-, 2-, 3-, 4-, 5- and 6-positions) catalyses the hydrolysis of myo-inositol 1,2,3,4,5,6-hexakisphosphate (phytic acid, $InsP_6$) to inorganic monophosphates and to free myo-inositol.

Many phytases hydrolyse only 5 phosphate bonds of phytic acid, i.e. 83% of the potential phosphorus. These enzymes hydrolyse phytic acid to myo-inositol monophosphate but not to free myo-inositol.

The expression "activity of the phytase" is intended to mean the enzymatic activity of the phytase. This activity is expressed in International Units (I.U.) per milligram of protein. One I.U. of enzymatic activity is the catalytic ability to convert one micromole of substrate per unit of time, at a given pH and at a given temperature.

Preferably, the first phytase has an optimum temperature of between 55° C. and 80° C. and an optimum pH of between pH 3.5 and pH 5.

In a preferred embodiment, the first phytase is a phytase of the yeast *Schwanniomyces castellii* or a phytase of the yeast *Debaryomyces castellii*.

In another particularly advantageous embodiment, the first phytase is the phytase of SEQ ID No. 1 or the phytase of SEQ ID No. 2.

The compositions according to the invention comprise at least a second phytase exhibiting at least 80% identity with the phytase of SEQ ID No. 3.

The phytase of SEQ ID No. 3 is a phytase of the filamentous fungus *Aspergillus niger*.

Preferably, the second phytase exhibits at least 80%, 90%, 95%, 98%, and preferably at least 99%, of amino acids that are identical with the phytase of SEQ ID No. 3.

Preferably, the second phytase conserves the properties and in particular the catalytic properties of the phytase of SEQ ID No. 3. Preferably, this phytase is isolated from other strains of *Aspergillus niger* or from other filamentous fungi. Alternatively, this phytase can be obtained by site-directed mutagenesis techniques, for example.

The expression "amino acids that are identical" is intended to mean amino acids which do not vary between two sequences. The second phytase can exhibit a deletion, an addition or a substitution of at least one amino acid with respect to the phytase of SEQ ID No. 3.

According to the invention, the second phytase used in the compositions and the methods of the invention therefore exhibits a degree of identity with the phytase of SEQ ID No. 3 and conserves the catalytic properties of the latter.

Preferably, the second phytase is a 3-phytase which catalyses the hydrolysis of at least five phosphate bonds of phytic acid.

Preferably, the second phytase has an optimum temperature of between 50° C. and 60° C. and an optimum pH of between pH 2 and pH 6. Even more preferably, the second phytase has a first optimum pH of between pH 2.5 and 3.5 and a second optimum pH of between pH 4.5 and 5.5.

In a preferred embodiment, the second phytase is an *Aspergillus niger* phytase.

In an advantageous embodiment, the second phytase is the phytase of SEQ ID No. 3.

The enzymatic activity of a phytase varies in particular as a function of the pH. Phytases thus have pH ranges (or spheres) in which their enzymatic activity is higher or optimal. The term "range" is intended to mean a given pH sphere or interval. Two phytases have enzymatic activities in complementary pH ranges when these phytases have an activity in different pH ranges. Preferably, these ranges overlap or partially superimpose. Typically, the phytases have a higher enzymatic activity at an acidic pH. Two phytases having complementary pH ranges have thus, for example, a maximum enzymatic activity between pH 2 and pH 4 for the first phytase and a maximum enzymatic activity between pH 4 and pH 6 for the second phytase. In the compositions and the methods of the present invention, the first and the second phytase preferably have complementary pH ranges or complementary optimum pHs. The compositions and the methods according to the invention thus allow hydrolysis of phytic acid in a wide pH range.

The methods of measuring and of identifying the degree of identity between polypeptides are known to those skilled in the art. Use may, for example, be made of Vector NTi 9.1.0, alignment program AlignX (Clustal W algorithm) (Invitrogen INFORMAX). Preferably, the default parameters are used.

The phytases of the compositions and methods according to the invention are isolated or purified from their natural environment. The phytases can be prepared by means of various methods. These methods are in particular purification from natural sources such as cells naturally expressing these phytases, production of recombinant phytases by appropriate host cells and subsequent purification thereof, production by chemical synthesis or, finally, a combination of these various approaches. These various methods of production are well known to those skilled in the art. Thus, the phytases used in the compositions and the methods of the present invention can be isolated from *Schwanniomyces castellii*, from *Debaryomyces castellii* or from *Aspergillus niger*. In another embodiment, the phytases of the present invention are isolated from recombinant host organisms.

Preferably, the compositions according to the invention consist of a nutritional additive for animals or of animal feed.

A subject of the invention is also the use of a composition according to the invention, for the manufacture of a nutritional additive for animals or of an animal feed.

The present invention therefore also relates to feed additives that provide a phytase activity. The provision of this type of enzymatic activity makes it possible to improve the digestibility of the feed and to improve its nutritional value.

The term "nutritional additive" is intended to mean a substance intentionally added to a feed, generally in small amounts, so as to improve its nutritional characteristics or its digestibility. The nutritional additives for animals can, for example, contain vitamins, mineral salts, amino acids and enzymes.

The present invention also relates to the animal feeds. These feeds are usually in the form of meals or of granules into which the additives according to the invention are incorporated. The term "feed" is intended to mean anything that can be used for feeding animals. For the intensive rearing of animals, the animal feeds usually comprise a nutritional base and nutritional additives. The term "nutritional base" is intended to mean that which constitutes most of the animal's food intake, consisting, by way of example, of a mixture of cereals, of proteins and of fats of animal and/or plant origin.

The nutritional bases for animals are suitable for the diet of these animals and are well known to those skilled in the art. Usually, these nutritional bases comprise, for example, maize, wheat, pea and soybean. These nutritional bases are suited to the needs of the various animal species for which they are intended. These nutritional bases may already contain nutritional additives such as vitamins, mineral salts and amino acids.

In a preferred embodiment, the invention relates to feeds for monogastric animals, and in particular for poultry and pigs. The poultry comprise in particular laying hens, chickens for meat, turkeys and ducks. The pigs comprise in particular growing and finishing pigs and also piglets.

A subject of the invention is also the use of a composition according to the invention, for increasing the availability of phytic phosphorus and improving the digestibility of animal feeds.

The compositions and the methods according to the invention combine a first phytase capable of hydrolysing all the phosphate bonds of phytic acid, chosen from *Schwanniomyces castellii* phytases and *Debaryomyces castellii* phytases, and a second phytase capable of hydrolysing at least five phosphate bonds of phytic acid and having an enzyme activity in a pH range complementary to the pH range of the first phytase.

FIGURES

FIG. 1: Comparison of the kinetics of hydrolysis of phytic acid at various pHs for the 6 phytases alone or combined in pairs. The results are expressed as % of theoretical phosphates released.

Figure 2:
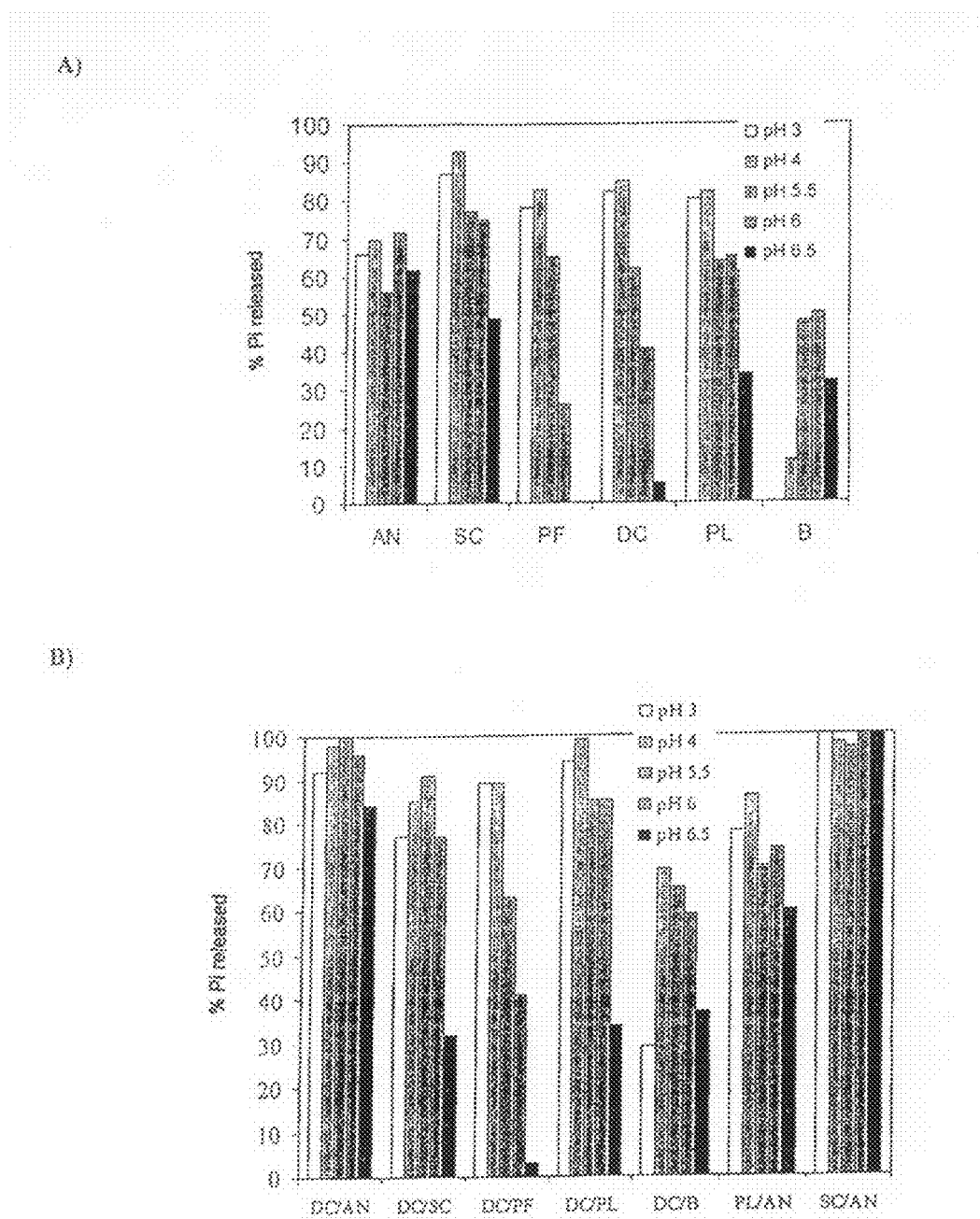

FIG. 2: Percentage hydrolysis of phytic acid by the various phytases after reaction for 120 minutes.

(A) phytases alone, (B) combined phytases. The dotted lines correspond to the hydrolysis of 5 phosphate bonds.

Figure 3:
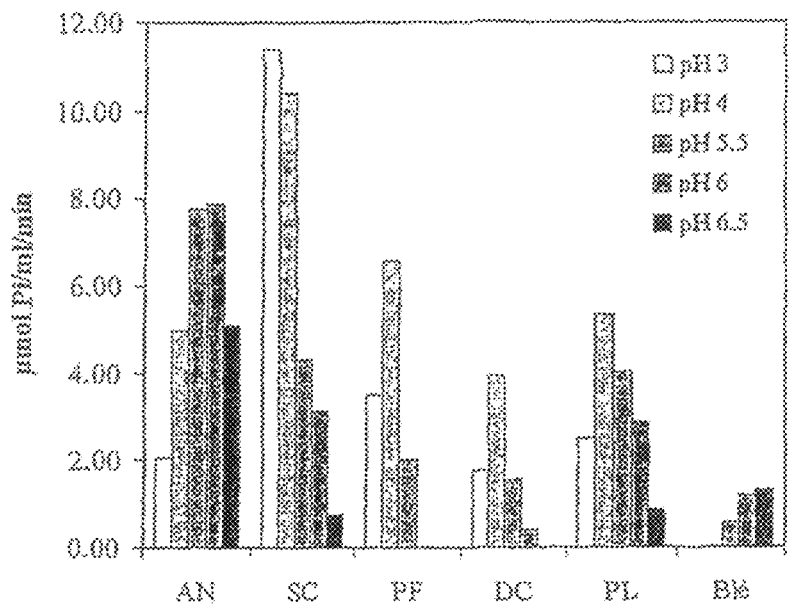
Figure 3:
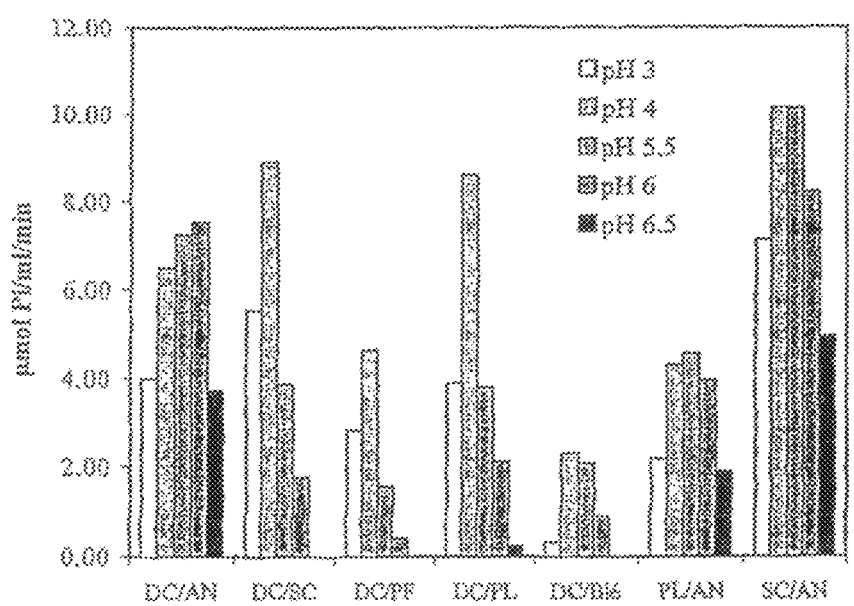

FIG. 3: Comparison of the initial rates of hydrolysis of phytic acid ($\mu$mol·ml$^{-1}$·min$^{-1}$) for 6 phytases at various pHs. (A) phytases alone, (B) combined phytases. The rates are calculated during the first 10 minutes of the reaction.

EXAMPLES

Materials and Methods

1. Phytase Origins

*Aspergillus niger* Natuphos (AN): batch R2503 or batch 057NPHO2 Wim van Hartingsveldt, Cora M. J. van Zeijl, G. Marian Harteveld, Robin J. Gouka, Marjon E. G. Suykerbuyk, Ruud G. M. Luiten, Peter A. van Paridon, Gerard C. M. Selten, Annemarie E. Veenstra, Robert F. M. van Gorcom and Cees A. M. J. van den Hondel; Cloning, characterization and overexpression of the phytase-encoding gene (phyA) of *Aspergillus niger*. Gene, 127, (1) 87-94 (1993)

*Peniophora lycii* (PL): batch 172NHSO2 Lassens, S. F., Breinholt, J., Ostergaard, P. R., Brugger, R., Bischoff, A., Wyss, M. and Fuglsang, C. C.; Expression, gene cloning, and characterization of five novel phytases from four basidiomycete fungi: *Peniophora lycii, Agrocybe pediades*, a *Ceriporia* and *Trametes pubescens*. Appl. Environ. Microbiol. 67 (10), 4701-4707 (2001)

*Penicillium funiculosum* (PF): Godo A1346 batch 1301 WO 03054199

Wheat (B): Sigma reference P1259. WO 0183763

*Schwanniomyces castellii* (SC): produced in *Candida boidinii* batch 10059 CN 25 EP 0931837

*Debaryomyces castellii* strain CBS 2923 (DC).

2. Enzymatic Method

The phytase activity is measured, by following the release of inorganic phosphate over time.

The activity is measured in the presence of 8 mM of sodium phytate (Sigma) dissolved in a 200 mM sodium acetate buffer, pH 5.5, at 37° C. (5 volumes). The reaction is triggered by the addition of the enzymatic extract (1 volume). The reaction is stopped by acidification of the medium with 20% trichloroacetic acid (1 volume of reaction medium+1 volume of acid). The amount of phosphate released is determined after various incubation times.

One enzymatic unit (U) is defined as the amount of enzyme which releases one $\mu$mole of inorganic phosphate in one minute.

3. Conditions for Hydrolysis of Phytates at Various pHs

The hydrolysis is carried out at 40° C. in 10 ml of 250 mM acetate buffer for pHs 4 to 6.5 or of 200 mM glycine buffer at pH 3, containing: 0.340 mM of sodium phytate, 0.04 or 0.08 U/ml of phytase. Samples are taken at various times for 120 minutes. The reaction is stopped by the addition of trichloroacetic acid.

The phosphates are assayed directly without dilution.

4. Phosphate Assay

The amount of phosphate released is visualized by colorimetry. The visualizing solution, prepared extemporaneously, contains iron sulphate (380 mM, 1 volume) and ammonium heptamolybdate (12 mM, 4 volumes). The absorbance is measured at 700 nm after visualization for 30 minutes at ambient temperature (1 volume of reaction medium+1 volume of visualizing solution), using a UV/visible spectrophotometer (Beckman DU 530).

A calibration line is established beforehand with potassium dihydrogen phosphate.

Results

1. Phytases Tested

The phytases tested differ from one another according to various criteria: (1) biochemical characteristics (optimum pH, stereospecificity: 3, 4, or 6 phytases), (2) number of phosphate bonds hydrolysed.

All these phytases have an optimum hydrolysis pH close to 5; however, the AN and PL phytases have a second optimum pH at 2.5. Three completely hydrolyse the phosphates (SC, DC, wheat). The position hydrolysed first is either the 3-position (AN, PL, DC) or the 6-position (PL), or the 4-position (wheat) (Table 1).

TABLE 1

Comparison of the biochemical characteristics of the phytases

| Origin | Km ($\mu$M) | Optimum pH | Optimum temperature (° C.) | Number of phosphate bonds hydrolysed | Stereospecificity (order of hydrolysis of phosphate bonds) |
|---|---|---|---|---|---|
| *Aspergillus niger*[1] | 40/27 | 2.5-5.5 | 55/58 | 5 | 3/4/5/6/1 |
| *Peniophora lycii*[1] | 33 | 2.5-5.5 | 58 | 5 | 6/3 (pH 5.5) 3.6 (pH 3 and 5.5) |
| *Penicillium funiculosum*[2] | 550 | 4-5 | 50 | 5 or 6 | 3/4 |
| Wheat[3] | 22 | 5-7 | 55 | 6 | 4/3/5/6/1/2 |
| *Schwanniomyces castellii*[4] | 38 | 4.4 | 77 | 6 | ? |

TABLE 1-continued

Comparison of the biochemical characteristics of the phytases

| Origin | Km (µM) | Optimum pH | Optimum temperature (° C.) | Number of phosphate bonds hydrolysed | Stereospecificity (order of hydrolysis of phosphate bonds) |
|---|---|---|---|---|---|
| Debaryomyces castellii | 236 | 4-4.5 | 60 | 6 | 3/4/5/6/1-2 |

[1]Ullah, A. H. J. and Sethumadhavan, K., (2003) PhyA gene product of *Aspergillus ficuum* and *Peniophora lycii* produces dissimilar phytases. Biochemical and Biophysical Research Communications 303: 463-468
[2]WO 03054199 filed Jun. 13, 2003 Bohlmann, R., Moussu, F., Nore, O., Pierrard, J., Saunier, D., Testeniere, O., New polynucleotide encoding fungal phytase, useful as feed additive to improve phosphate assimilation, also new strain of *Penicillium*.
[3]Nakano, T., Joh, T., Narita, K., Hayakawa, T. (2000) The pathway of dephosphorylation of myo-Inositol Hexakisphosphate by Phytases from Wheat Bran of *Tricicum aestivum* L. cv Nourin#61. Biosci. Biotechnol. Biochem., 64: 995-1003
[4]Segueilha, L., Lambrechts, C., Boze, H., Moulin, G. and Galzy, P. (1992) Purification and Properties of the Phytase from *Schwanniomyces castellii*. J. Ferment. Bioeng. 74(1): 7-11.

2. Comparison of the Effectiveness of Phytic Acid Hydrolysis by 6 Phytases at Various pHs The study is carried out in the presence of 0.340 mM of phytate. The amount of enzyme introduced corresponds to 0.08 U/ml of phytase, measured under standard conditions at pH 5.5. The pH values tested are 3, 4, 5.5, 6, 6.5. The reaction is followed for 120 minutes. Samples are taken over time, the reaction is stopped by acidification, and the phosphates are assayed by colorimetry.

The comparison of the various phytases is carried out as a function of the hydrolysis efficiency, i.e. the percentage of phosphate released relative to the theoretical percentage. The results are expressed in FIG. 1A.

According to the literature, 4 phytases (PF, SC, DC, B) are capable of completely hydrolysing phytic acid to inositol and phosphate; 2 phytases (AN and PL) hydrolyse only 5 bonds, i.e. 83% of the potential phosphorus.

Under the conditions tested at pH 3 and pH 4, 4 phytases (SC, PF, DC and PL) hydrolyse at least 80% of the phytic acid. The wheat phytase is not very active at pH 3 and pH 4. For pH values above pH 5.5, no phytase hydrolyses more than 70% of the phytic acid.

The PF and DC phytases are not very active at pH 6.5. The AN phytase is the least sensitive to variations in pH; however, it releases only 60 to 70% of the phosphates, i.e. values 10 to 20% lower than those expected (FIG. 2A).

The comparison of the initial rates of phosphate release show a great deal of heterogeneity between the phytases (FIG. 3A). The most efficient phytase at acidic pH is that of *Schwanniomyces castellii*, whereas that of *A. niger* is the most efficient at pH values above 5.5. The wheat phytase is the least efficient irrespective of the conditions tested.

3. Influence of pH on the Rate of Phosphate Release in The Presence of Combined Phytases In order to improve the efficiency of phytic acid hydrolysis, several combinations of two phytases are tested. Each phytase is introduced at 0.04 U/ml, i.e. a total value of 0.08 U/ml in the reaction tube. The DC phytase, which hydrolyses 6 phosphate bonds, is systematically tested in combination with the other phytases, which hydrolyse 5 or 6 phosphate bonds. Two other combinations are also used to compare, firstly, another combination of phytases able to release 6 and 5 phosphates (SC/AN) and, secondly, two phytases, PL/AN, having very similar biochemical characteristics (FIG. 1B).

An overall analysis makes it possible to show that the combination of 2 phytases mostly promotes the efficiency of phytic acid hydrolysis. Although, under the same conditions, no phytase completely hydrolyses phytic acid, for 2 mixtures (DC/AN and SC/AN), 100% to 85% of the phosphate bonds are hydrolysed whatever the pH. For the DC/PL combination, a gain of approximately 20% at acidic pHs is also observed. The PL/AN, DC/PF and DC/SC combinations provide little improvement (FIG. 2B).

The comparison of the initial hydrolysis rates shows that a strong synergistic effect exists for the SC/AN combination and for the DC/AN combination compared with the phytases alone and compared with the other phytase combinations. The pH-related differences in hydrolysis rate are minimized when the combination is used. The other combinations are less efficient, the synergistic effect is visible only for certain pHs, for example for DC/PL at pH 3 and pH 4 (FIG. 3).

The synergistic effect appears to be due, to a large extent, to the ability of the phytases to hydrolyse all the phosphates. In addition, the best combinations concern phytases having complementary optimum pHs for activity (2.5-4.5). It should, however, be noted that there is little synergistic effect for the phytases that are the least effective in terms of hydrolysis efficiency, such as that of wheat and of *Penicillium funiculosum*.

4. Influence of the Concentrations and of the Proportion of Phytases on the Efficiency of Phytic Acid Hydrolysis We compared the influence of the amount of phytase (dose effects) and of the proportion of the mixture of phytases on phytic acid hydrolysis. Three combinations were used, DC/AN, DC/PL and AN/PL, and 2 phytase concentrations (0.04 and 0.08 U/ml) were tested (Tables 2 and 3).

TABLE 2

Comparison of the percentage phytic acid hydrolysis for the various combinations, tested at two final concentrations, 0.04 and 0.08 U/ml. The first three columns give the values for the three phytases alone at the concentration 0.08 U/ml.

|  | AN (0.08 U) | DC (0.08 U) | PL (0.08 U) | AN/DC (0.08 U) | AN/DC (0.04 U) |
|---|---|---|---|---|---|
| pH 3 | 66 | 82 | 80 | 92 | 67 (73%) |
| pH 4 | 69 | 85 | 83 | 95 | 96 (101%) |
| pH 5.5 | 55 | 63 | 67 | 92 | 81 (87%) |
| pH 6 | 72 | 42 | 64 | 94 | 78 (83%) |
| pH 6.5 | 63 | 6 | 34 | 75 | 42 (56%) |

TABLE 2-continued

Comparison of the percentage phytic acid
hydrolysis for the various combinations, tested at two
final concentrations, 0.04 and 0.08 U/ml. The first
three columns give the values for the three phytases
alone at the concentration 0.08 U/ml.

|  | PL/DC (0.08 U) | PL/DC (0.04 U) | AN/PL (0.08 U) | AN/PL (0.04 U) |
|---|---|---|---|---|
| pH 3 | 94 | 70 (74%) | 79 | 56 (72%) |
| pH 4 | 100 | 93 (94%) | 86 | 76 (89%) |
| pH 5.5 | 85 | 71 (84%) | 70 | 66 (94%) |
| pH 6 | 85 | 47 (56%) | 74 | 67 (90%) |
| pH 6.5 | 35 | 10 (30%) | 61 | 52 (86%) |

The values between parentheses represent the ratio of the values obtained with 0.04 U/ml to those in the presence of 0.08 U/ml.

The percentages of hydrolysis during the study with the mixture of enzymes (overall concentration 0.08 U/ml) are higher than those determined with the enzymes alone (0.08 U/ml) and close to 100% for the AN/DC and PL/DC mixtures, in a pH range varying from 3 to 6. The AN/PL mixture does not significantly increase the percentage hydrolysis observed with each phytase taken separately. The 2-fold reduction of the overall amount provided (0.04 U/ml) does not induce a 2-fold decrease in released phosphates. In certain cases, AN/DC and PL/DC at pH 4 and pH 5.5, and AN/PL at pHs 4 to 6, the percentages of hydrolysis are equivalent to those observed in the presence of 0.08 U/ml (Table 3).

TABLE 3

Comparison of the initial rates of hydrolysis
(μmol/ml/min) of phytic acid for the various
combinations, tested at two final concentrations 0.04
and 0.08 U/ml.
The first three columns give the values for the three
phytases alone at the concentration 0.08 U/ml.

|  | AN (0.08 U) | DC (0.08 U) | PL (0.08 U) | AN/DC (0.08 U) | AN/DC (0.04 U) |
|---|---|---|---|---|---|
| pH 3 | 2.04 | 1.78 | 2.52 | 4.00 | 1.70 (42%) |
| pH 4 | 4.98 | 3.96 | 5.36 | 6.49 | 2.85 (44%) |
| pH 5.5 | 7.76 | 1.56 | 4.00 | 7.26 | 1.86 (26%) |
| pH 6 | 7.91 | 0.39 | 2.87 | 7.53 | 1.04 (14%) |
| pH 6.5 | 5.09 | 0.00 | 0.85 | 3.71 | 0.26 (7%) |

|  | PL/DC (0.08 U) | PL/DC (0.04 U) | AN/PL (0.08 U) | AN/PL (0.04 U) |
|---|---|---|---|---|
| pH 3 | 3.88 | 1.45 (37%) | 2.18 | 1.60 (73%) |
| pH 4 | 8.61 | 3.33 (39%) | 4.29 | 2.73 (63%) |
| pH 5.5 | 3.79 | 0.85 (22%) | 4.56 | 2.82 (62%) |
| pH 6 | 2.10 | 0.04 (2%) | 3.96 | 2.60 (66%) |
| pH 6.5 | 0.22 | 0.00 (0%) | 1.89 | 0.74 (39%) |

The values between parentheses represent the ratio of the rates obtained with 0.04 U/ml to those in the presence of 0.08 U/ml.

The combination of phytase therefore makes it possible to decrease the amount of phytase in the reaction medium by a factor two, while maintaining an identical hydrolysis efficiency, within a broad pH range. There is a clear dose effect on the release of phosphate.

On the other hand, the initial rates of phytic acid hydrolysis are at least two times lower in the presence of 0.04 U/ml of phytase than in the presence of 0.08 U/ml (Table 3). These results support the hypothesis that the synergy between the phytases essentially allows complete hydrolysis of the phosphates present.

The proportion of each phytase in the reaction medium does not appear to have a great deal of influence on the hydrolysis efficiency (Table 4). In all the cases, an increase in the amount of phosphate released is observed, with a slight advantage for a combination containing 50% of each phytase, mainly for pHs above 5.5.

TABLE 4

Comparison of the percentage phytic acid
hydrolysis as a function of the proportion of each
phytase in the mixture. In all cases, the overall
amount remains 0.08 U/ml.

| Proportion of phytases | AN | DC | AN/DC (1/1) | AN/DC (1/2) | AN/DC (2/1) |
|---|---|---|---|---|---|
| pH 3 | 66 | 82 | 92 | 90 | 88 |
| pH 4 | 69 | 85 | 95 | 93 | 93 |
| pH 5.5 | 55 | 63 | 92 | 79 | 79 |
| pH 6 | 72 | 42 | 94 | 87 | 86 |
| pH 6.5 | 63 | 6 | 75 | 52 | 64 |

Under our experimental conditions, no phytase completely hydrolyses phytic acid to inositol and phosphates, although 4 of them are capable of releasing all the phosphates according to the literature. Four phytases SC, PF, DC and PL, hydrolyse 80% of the phosphate bonds at pH values of 3 and 4. Two mixtures, DC/AN and SC/AN, hydrolyse from 80% to 100% of the phosphate, bonds at all the pHs tested.

The combination of phytase of 3-phytase (AN, DC, PF), 4-phytase (B) or 6-phytase (PL) type, with one another, does not provide any notable improvement.

The complementation and the synergy between phytases appears to depend on 2 criteria specific to each phytase: (1) on their profile of activity as a function of pH, (2) on their ability to hydrolyse, or not, all the phosphates.

The use of such combinations in animal nutrition could make it possible to decrease the amounts of phytases used by at least 20% and therefore to reduce costs. The content of phosphate of phytic origin in the feed would also be increased, improving the food value and thus making it possible to decrease the intake of inorganic phosphate. The pollution caused by unavailable phosphate waste would thus be decreased.

The invention claimed is:

1. A composition combining at least two 3-phytases for hydrolysis of phytic acid (myo-inositol 1,2,3,4,5,6-hexakisphosphate), comprising:
   a) a first phytase exhibiting at least 95% identity with the phytase of SEQ ID NO: 1 or exhibiting at least 95% identity with the phytase of SEQ ID NO: 2;
   b) a second phytase exhibiting at least 95% identity with the phytase of SEQ ID NO: 3.
   wherein the first and second phytases have a synergistic hydrolysis effect on phytic acid in the absence of a phytase having a different stereospecificity.

2. The composition according to claim 1, wherein the first phytase is a 3-phytase which catalyses the hydrolysis of the six phosphate bonds of phytic acid.

3. The composition according to claim 1, wherein the first phytase has an optimum temperature of between 55° C. and 80° C. and an optimum pH of between pH 3.5 and pH 5.

4. The composition according to claim 1, wherein the first phytase is a phytase of the yeast *Schwanniomyces castellii* or a phytase of the yeast *Debaryomyces castellii*.

5. The composition according to claim 1, wherein the first phytase is the phytase of SEQ ID NO: 1 or the phytase of SEQ ID NO: 2, and the second phytase is the phytase of SEQ ID NO: 3.

6. The composition according to claim 1, wherein the second phytase is a 3-phytase which catalyses the hydrolysis of at least five phosphate bonds of phytic acid.

7. The composition according to claim 1, wherein the second phytase has an optimum temperature of between 50° C. and 60° C. and an optimum pH of between pH 2 and pH 6.

8. The composition according to claim 1, wherein the second phytase is an *Aspergillus niger* phytase.

9. The composition according to claim 1, wherein the first phytase exhibits at least 99% identity with the phytase of SEQ ID NO: 1 or exhibits at least 99% identity with the phytase of SEQ ID NO: 2, and the second phytase exhibits at least 99% identity with the phytase of SEQ ID NO: 3.

10. The composition according to claim 1, wherein said composition is in the form of a nutritional additive for animals or of an animal feed.

11. A method for supplementing the nutrition of an animal comprising feeding said animal the composition of claim 1 in a nutritional additive for animals or in an animal feed.

12. A method for increasing the availability of phytic phosphorus and improving the digestibility of animal feeds, comprising feeding animals the composition of claim 1.

13. A method of hydrolysis of phytic acid (myo-inositol 1,2,3,4,5,6-hexakisphosphate) to inorganic monophosphates, to myo-inositols with a lower degree of phosphorylation and to free myo-inositol, comprising:
   hydrolyzing phytic acid with a first phytase and a second phytase,
   the first phytase exhibiting at least 95% identity with the 3-phytase of SEQ ID NO: 1 or exhibiting at least 95% identity with the 3-phytase of SEQ ID NO: 2, and
   the second phytase exhibiting at least 95% identity with the 3-phytase of SEQ ID NO: 3,
   wherein the first and second phytases have a synergistic hydrolysis effect on phytic acid in the absence of a phytase having a different stereospecificity.

14. The method according to claim 13, wherein the first phytase is a 3-phytase which catalyses the hydrolysis of the six phosphate bonds of phytic acid.

15. The method according to claim 13, wherein the first phytase has an optimum temperature of between 55° C. and 80° C. and an optimum pH of between pH 3.5 and pH 5.

16. The method according to claim 13, wherein the first phytase is a phytase of the yeast *Schwanniomyces castellii* or a phytase of the yeast *Debaryomyces castellii*.

17. The method according to claim 13, wherein the first phytase is the phytase of SEQ ID NO: 1 or the phytase of SEQ ID NO: 1 and the second phytase is the phytase of SEQ ID NO: 3.

18. The method according to claim 13, wherein the second phytase is a 3-phytase which catalyses the hydrolysis of at least five phosphate bonds of phytic acids.

19. The method according to claim 13, wherein the second phytase has an optimum temperature of between 50° C. and 60° C. and an optimum pH of between pH 2 and pH 6.

20. The method according to claim 13, wherein the second phytase is an *Aspergillus niger* phytase.

21. The method according to claim 13, wherein the first phytase exhibits at least 99% identity with the phytase of SEQ ID NO: 1 or exhibits at least 99% identity with the phytase of SEQ ID NO: 2, and the second phytase is the exhibits at least 99% identity with the phytase of SEQ ID NO: 3.

22. A kit or assembly for feeding animals, comprising:
the *Schwanniomyces castellii* 3-phytase of SEQ ID NO: 1 or the *Debaryomyces castellii* 3-phytase of SEQ ID NO: 2; and
the *Aspergillus niger* 3-phytase of SEQ ID NO: 3,
wherein the *Schwanniomyces castellii* 3-phytase of SEQ ID NO: 1 or the *Debaryomyces castellii* 3-phytase of SEQ ID NO: 2, in combination with the *Aspergillus niger* 3-phytase of SEQ ID NO: 3, have a synergistic hydrolysis effect on phytic acid in the absence of a phytase having a different stereospecificity.

23. The method according to claim 13, wherein phytic acid is completely hydrolyzed.

24. The composition according to claim 1, wherein the synergistic hydrolysis effect on phytic acid is obtained over a pH range of 3-6.5.

25. The composition according to claim 1, wherein the first phytase is the phytase exhibiting at least 95% identity with the phytase of SEQ ID NO: 2.

26. The method according to claim 13, wherein the first phytase is the phytase exhibiting at least 95% identity with the phytase of SEQ ID NO: 2.

27. The kit or assembly according to claim 22, wherein the kit or assembly comprises the *Debaryomyces castellii* 3-phytase of SEQ ID NO: 2, and wherein the *Debaryomyces castellii* 3-phytase of SEQ ID NO: 2, in combination with the *Aspergillus niger* 3-phytase of SEQ ID NO: 3, have a synergistic hydrolysis effect on phytic acid in the absence of a phytase having a different stereospecificity.

* * * * *